(12) United States Patent
Jayaraman et al.

(10) Patent No.: US 9,696,132 B2
(45) Date of Patent: Jul. 4, 2017

(54) TUNABLE LASER ARRAY SYSTEM

(71) Applicants: Praevium Research, Inc., Santa Barbara, CA (US); Thorlabs, Inc., Newton, NJ (US)

(72) Inventors: Vijaysekhar Jayaraman, Goleta, CA (US); Christopher Burgner, Santa Barbara, CA (US); Demis John, Goleta, CA (US); Benjamin Michael Potsaid, Cambridge, MA (US); Alex Ezra Cable, Newton, NJ (US)

(73) Assignees: Praevium Research, Inc., Santa Barbara, CA (US); Thorlabs, Inc., Newton, NJ (US)

( * ) Notice: Subject to any disclaimer, the term of this patent is extended or adjusted under 35 U.S.C. 154(b) by 282 days.

(21) Appl. No.: 14/214,425

(22) Filed: Mar. 14, 2014

(65) Prior Publication Data

US 2014/0268050 A1 Sep. 18, 2014

Related U.S. Application Data

(60) Provisional application No. 61/793,604, filed on Mar. 15, 2013.

(51) Int. Cl.
*A61B 3/14* (2006.01)
*A61B 3/00* (2006.01)
(Continued)

(52) U.S. Cl.
CPC ........ *G01B 9/02004* (2013.01); *A61B 3/0008* (2013.01); *A61B 3/102* (2013.01);
(Continued)

(58) Field of Classification Search
CPC .. A61B 3/14; A61B 3/12; A61B 3/103; A61B 3/1225; A61B 3/032; A61B 3/1015
(Continued)

(56) References Cited

U.S. PATENT DOCUMENTS 5,754,578 A 5/1998 Jayaraman
6,227,724 B1 5/2001 Verdiell
(Continued)

FOREIGN PATENT DOCUMENTS

EP 0395315 A2 10/1990
EP 2701249 A2 2/2014
(Continued)

OTHER PUBLICATIONS

International Search Report mailed Sep. 18, 2014 in corresponding international application No. PCT/US2014/029458.
(Continued)

*Primary Examiner* — Dawayne A Pinkney
(74) *Attorney, Agent, or Firm* — Graham Curtin, P.A.

(57) ABSTRACT

A system for swept source optical coherence tomography, the system including a light source emitting multiplexed wavelength-swept radiation over a total wavelength range, the light source including N wavelength-swept vertical cavity lasers (VCL) emitting N tunable VCL outputs having N wavelength trajectories, a combiner for combining the N tunable VCL optical outputs into a common optical path to create the multiplexed wavelength-swept radiation, a splitter for splitting the multiplexed wavelength-swept radiation to a sample and a reference path, an optical detector for detecting an interference signal created by an optical interference between a reflection from the sample and light traversing the reference path, and a signal processing system which uses the interference signal to construct an image of the sample, wherein at least one of the N wavelength trajectories differs from another of the N wavelength trajectories with respect to at least one parameter.

33 Claims, 12 Drawing Sheets

(51) Int. Cl.
*A61B 3/10* (2006.01)
*G01B 9/02* (2006.01)
*H01S 5/183* (2006.01)
*H01S 5/42* (2006.01)
*H01S 5/06* (2006.01)
*H01S 5/40* (2006.01)
*H01S 5/30* (2006.01)
*H01S 5/20* (2006.01)

(52) U.S. Cl.
CPC ..... *G01B 9/02007* (2013.01); *G01B 9/02091* (2013.01); *H01S 5/18366* (2013.01); *H01S 5/4087* (2013.01); *H01S 5/0607* (2013.01); *H01S 5/18308* (2013.01); *H01S 5/18311* (2013.01); *H01S 5/18341* (2013.01); *H01S 5/18369* (2013.01); *H01S 5/18372* (2013.01); *H01S 5/18377* (2013.01); *H01S 5/2059* (2013.01); *H01S 5/3095* (2013.01); *H01S 5/4012* (2013.01); *H01S 5/423* (2013.01)

(58) Field of Classification Search
USPC ....... 351/206, 200, 205, 208–210, 221, 243, 351/246
See application file for complete search history.

(56) References Cited

U.S. PATENT DOCUMENTS

| | | | |
|---|---|---|---|
| 6,741,629 | B1 | 5/2004 | Garnache et al. |
| 2002/0074631 | A1 | 6/2002 | Sato et al. |
| 2002/0075929 | A1 | 6/2002 | Cunningham et al. |
| 2002/0126725 | A1 | 9/2002 | Tayebati |
| 2003/0169786 | A1 | 9/2003 | Kapon et al. |
| 2003/0231664 | A1 | 12/2003 | Geske |
| 2007/0183643 | A1 | 8/2007 | Jayaraman |
| 2011/0261849 | A1 | 10/2011 | Shinagawa et al. |
| 2013/0016360 | A1 | 1/2013 | Ensher et al. |
| 2013/0044772 | A1 | 2/2013 | Ensher et al. |
| 2014/0028997 | A1* | 1/2014 | Cable ............. G01B 9/02091 356/51 |

FOREIGN PATENT DOCUMENTS

| | | |
|---|---|---|
| WO | 2005122349 A1 | 12/2005 |
| WO | 2011121962 A1 | 10/2011 |
| WO | 2012092190 A1 | 7/2012 |
| WO | 2014018939 A2 | 1/2014 |
| WO | 2014018950 A1 | 1/2014 |

OTHER PUBLICATIONS

V. Jayaraman, J. Jiang, B. Potsaid, G. Cole, J Fujimoto, and A. Cable "Design and performance of broadly tunable, narrow linewidth, high repetition rate 1310nm VCSELs for swept source optical coherence tomography," SPIE vol. 8276 paper 82760D, 2012.

G.D. Cole, J.E. Bowers, K.L. Turner, and N.C. McDonald, "Dynamic Characterization of MEMs-Tunable Vertical-Cavity SOAs," IEEE/LEOS International Conference on Optical MEMS and Their Applications (MOEMS 2005), Oulu, Finland, Aug. 1-4, 2005.

V. Jayaraman, G.D. Cole, M. Robertson, A. Uddin, and A. Cable, "High Sweep Rate 1310nm MEMS-VCSEL with a 150nm continuous tuning range," Electronics Letters, May 5, 2012.

V. Jayaraman, G.D. Cole, M. Robertson, C. Burgner, D. John, A. Uddin, and A. Cable, "Rapidly-swept Ultra-5 widely tunable 1060nm MEMS-VCSELs," Electronics Letters, Sep. 6, 2012.

V. Jayaraman, T.J. Goodnough, T.L. Beam, F.M. Ahedo, and R.A. Maurice, "Continuous wave operation of single transverse mode 1310nm VCSEL up to 115C," IEEE Photonics Technology Letters vol. 12, No. 12, Dec. 2000.

M. Nakahama, T. Shimada, and F. Koyama, "Lateral Integration of MEMS-VCSEL and slow light amplifier boosting single mode power," IEICE Electronics Express, vol. 9, No. 6, pp. 544-551, 2012.

Supplementary European search report including the European search opinion issued for corresponding European Patent Application No. 14 764 914.9 dated Oct. 14, 2016.

V. Jayaraman, J. Jiang, B. Potsaid, G. Cole, J Fujimoto, and A. Cable "Design and performance of broadly tunable, narrow linewidth, high repetition rate 1310nm VCSELs or swept source optical coherence tomography," SPIE vol. 8276 paper 82760D, 2012.

International Search Report with Written Opinion, mailed Sep. 11, 2014, for corresponding international application PCT/US2014/029632.

* cited by examiner

A. VCL Drive Current

B. VCL Tuning Signal

C. Multiplexed output wavelength

Legend

——————— VCL 1

– – – – – – – VCL 2

TUNABLE LASER ARRAY SYSTEM

CROSS REFERENCES TO RELATED APPLICATIONS

This application claims the benefit of U.S. Provisional Patent Application No. 61/793,604 filed on Mar. 15, 2013. The disclosure of U.S. Provisional Patent Application 61/793,604 is hereby incorporated by reference.

FIELD OF THE INVENTION

This invention relates generally to tunable lasers and tunable laser applications, material or sample characterization, material or sample modification, optical coherence tomography, spectroscopy, sensors, measurement, communications, and vertical cavity lasers.

BACKGROUND

Wavelength tunable lasers and widely tunable lasers are integral components of a range of instruments, devices, and tools use for characterizing or modifying materials, objects, or samples. Wavelength tunable lasers and widely tunable lasers are also used in sensors and for data transmission and communication. In many applications, the wavelength is tuned continuously (e.g. the wavelength is swept in time) and possibly according to a desired tuning profile. In other applications, the laser is tuned to a specific wavelength and parked or held predominately stationary at that wavelength for a length of time. There exists a need for highly flexible and configurable tunable or swept laser sources that can be adapted to the specific needs of a multitude of applications. Described here is a Laser Array that consists of a series of laser sources that are chosen to have specific properties so as to enable the Laser Array to be applied to a range of applications with improved performance or additional capability. Applications the Laser Array can be applied to include, but are not limited to: interventional medicine, basic research, biological research, laser based spectroscopy, medical imaging, biological imaging, industrial imaging, material characterization, morphological characterization of a sample, sample modification, sample stimulation, optical sensors, environmental sensors, health sensors, optical sensing, optical signal generation, data transmission, data communication, and interferometric measurement. The center wavelength for these Laser Arrays covers the entire optical spectrum from the deep UV to the Far IR, with the tuning range covering a few percent of the center wavelength out to tuning ranges of substantially more than a full octave. These examples are a subset of the multitude of applications where lasers, and more specifically tunable lasers have been found to be beneficial and it is understood that the current invention applies more generally beyond the specific applications stated.

Although certain embodiments of the present invention can be used in a wide range of applications, it is helpful to consider the embodiments in the context of a specific application. Optical coherence tomography (OCT) is an optical imaging technique that can be implemented using a wavelength tunable laser. Optical coherence tomography (OCT) is a non-invasive imaging technique that can provide high-resolution depth profiling or morphological characterization of a sample below or at the sample surface. OCT can also provide information about dynamic processes occurring in the sample by Doppler OCT, spectroscopic information about the sample by spectroscopic OCT, polarization and birefringent information about the sample through polarization sensitivity OCT, and precision measurements of deflection or motion through intensity and phase sensitive OCT. OCT will be used to provide an in-depth look at the benefits provided by the Laser Array described in this work. To add additional clarity examples will be presented based on the use of a VCL device, it should be understood that any tunable laser could be substituted for the VCL. In recent years, swept source optical coherence tomography (SSOCT) using wavelength swept lasers has demonstrated superior imaging quality, superior imaging range, and superior imaging speed relative to time domain and spectral domain OCT systems. The Microelectromechanical systems (MEMS)-tunable vertical cavity laser (MEMS-VCL) is expected to be a key swept source in emerging SSOCT systems, because of its truly single-mode mode-hop-free operation enabling long coherence lengths, and because of the short cavity and low MEMS mirror mass enabling MHz wavelength scanning rates. These advantages are described in (V. Jayaraman, J. Jiang, B. Potsaid, G. Cole, J Fujimoto, and A. Cable "Design and performance of broadly tunable, narrow linewidth, high repetition rate 1310 nm VCSELs for swept source optical coherence tomography," SPIE volume 8276 paper 82760D, 20112.). Prior art OCT systems employing one VCL as a swept source have enabled MHZ rates and >100 nm wavelength sweep range. Nevertheless the imaging rates and sweep trajectories remain limited by the mechanical resonance and dynamic properties of a single MEMS actuator, and wavelength sweep range remains limited by the gain-bandwidth of a single semiconductor gain medium. Prior art OCT systems have also employed a MEMS-VCSEL with flat frequency response, enabling variable wavelength sweep rate in a single VCL and linearization of the sweep trajectory through adding harmonics of the fundamental drive frequency. In some applications, however, it is advantageous to operate at the MEMS mechanical resonance of the device, to take advantage of low voltage operation in a vacuum environment, as described (G. D. Cole, J. E. Bowers, K. L. Turner, and N. C. McDonald, "Dynamic Characterization of MEMs-Tunable Vertical-Cavity SOAs," IEEE/LEOS International Conference on Optical MEMS and Their Applications (MOEMS 2005), Oulu, Finland, 1-4 Aug. 2005.)

From the foregoing, it is clear that there is significant benefit to a light source that could be used in a SS-OCT system employing MEMS-VCL or other laser technology in which sweep speed is not limited by MEMS mirror mechanical resonance, wavelength tuning range is not limited by gain bandwidth of a single semiconductor gain medium, and which exploits low voltage and possibly resonant operation.

SUMMARY OF THE INVENTION

A wavelength tunable laser is a laser that can tune the wavelength or optical frequency of output emission (FIG. 1), the tuning can be continuous over a defined range, the tuning could be achieved in a stepped manner, or any combination of the two. The wavelength tuning could be realized using a tunable filter element incorporated into the individual laser, or tuning could be realized by using the inherent wavelength dependence of external factors such as temperature, drive current, or atmospheric pressure. A widely tunable laser is a tunable laser that can be tuned over abroad wavelength band. The wavelength tunability of the laser is useful for a range of applications that may characterize a sample, modify a sample permanently, or affect a sample, such as spectroscopy, atomic or molecular excitation, Optical coherence tomography (OCT) imaging, ablation, thermal stimulation, heating, moving, thermally shocking, fluorescent excitation, or depletion (FIG. 2). Tunable lasers are used in (Light Detection and Ranging (LIDAR) systems. The wavelength tunability of the laser may also be useful as an input to an optical sensor using either a free space or fiber optic design (FIG. 2). The wavelength tunability of the laser can also be used as part of a data or communications link (FIG. 2).

An embodiment of the present invention employs an array of at least two lasers, in which the outputs of the lasers in the array are multiplexed into an optical system (FIG. 3). While it is understood that the individual sources or light are lasers in the general invention, there are advantages to a VCL design for constructing laser arrays. While it is understood that the present invention includes embodiments using non-VCL sources, in one embodiment, the present invention employs an array of at least two tunable vertical cavity lasers (VCLs), in which the outputs of the VCLs in the array are multiplexed into an optical system (FIG. 4). One embodiment of the present invention employs an array of at least two tunable vertical cavity lasers (VCLs), in which the outputs of the VCLs in the array are multiplexed into a common optical fiber, creating multiplexed wavelength-swept radiation with superior properties over using a single VCL alone. The outputs of the VCLs may also be multiplexed into a free space optical system, or the system may utilize some combination of free space and optical fiber. One preferred embodiment of this invention employs an array of VCLs driven by phase-translated copies of a single drive waveform, enabling multiplication of scan rate above that possible with one VCL, along with superior duty cycle. Similarly, through the introduction of dedicated drivers for each VCL, it is also possibly drive each VCL with a custom waveform to achieve a scan rate above that possible with one VCL, but with improved sweep trajectory characteristics. Another embodiment employs VCLs operating at different wavelength ranges enabling wider effective sweep range when VCLs are multiplexed together. In other embodiments, different VCLs of the array have different mechanical resonances or are driven over different bandwidths to enable resonant operation in conjunction with variable sweep rate for long range and short range imaging with a single device. The VCLs may also be operated off-resonance. More generally, further flexibility is realized by shaping the various electrical or optical drive waveforms for one or more of the VCLs. Combining the control of the shape of the tuning curve for one or more of the individual VCLs with the control of the wavelength range, sweep speed in units of wavelength per unit time, and repetition rates before or during use allows the VCL system to be optimized on the fly for changing conditions of the sample or the environment surrounding the sample. For electrically pumped VCLs (FIG. 4), the output emission power and wavelength tuning trajectory can be controlled by controlling the electrical inputs to the VCL. For optically, pumped VCLs (FIG. 5), the output emission power and wavelength tuning trajectory can be controlled by controlling the pump power and electrical signal to the actuator in the VCL, respectively. An optical amplifier can be used to amplify the power output of the VCL array (FIG. 6). Increasing the output of a VCL or controlling the power of the VCL using an optical amplifier is important for many applications of wavelength tunable lasers. For example, one application of wavelength swept lasers is OCT imaging, where large output powers can be desirable for high instrument sensitivity and it is preferable to control the output power as a function of wavelength. An optical amplifier can be used for both electrically pumped (FIG. 6) and optically pumped (FIG. 7) embodiments. The electrical or optical input to the optical amplifier can be controlled to dynamically affect the output power as a function of time of the laser array. It is also possible in some applications to use the output from the multiple VCL arrays without optical amplification when high output power and control of the output power are not needed.

As stated above, further flexibility is realized by shaping the various electrical or optical drive waveforms for one or more of the VCLs, it is understand that there are a multitude of devices unrelated to the basic laser array that can also be utilized to dynamically modify the optical output of the individual lasers that comprise the laser array. For example an electro-optic modulator drawn from a broad range of modulators known in the optical sciences could be used to advantageously control the wavelength, polarization, intensity, coherence, or any other property typically controlled with such devices. This invention differs substantially from other systems that utilize a collection of lasers, for example a bank of optical telecom DFB or tunable semiconductor backup lasers, in that this invention synchronizes the control of specific performance characteristics of each laser within the system so as to create a multi-laser system that has extended performance beyond the performance of the individual laser. The characteristics being controlled are any of the specifications of the lasers within the array that are influenceable in a controlled manner. This control allows for the laser array of this work to be used to carry out complex tasks in a manner superior to that of a single laser. Unlike a backup laser bank that is a collection of lasers that stands as a ready replacement for a failed laser. In contrast to this invention which involves the systematic control of the lasers within the array so as to extend the performance of the laser array, one such example being the combination of multiple lasers so as to provide an extended tuning range. More generally this laser array can be used to carry out complex functions as has been described within this work. The present invention provides a level of performance not possible with pre-existing laser systems, by combining a series of lasers whose performance specifications complement each other, along with electrical, electronic, and processor controls that allow the complimentary features to be stitched together, or combined in some manner, make it possible to utilize this laser array in optical systems with result that heretofore were not obtainable.

One embodiment of the present invention is a swept source optical coherence tomography system. The system comprises a light source emitting multiplexed wavelength-swept radiation over a total wavelength range. The light source comprises N wavelength-swept vertical cavity lasers (VCL) emitting N tunable VCL outputs having N wavelength trajectories, where N is greater than one, a combiner for combining the N tunable VCL optical outputs into a common optical path to create multiplexed wavelength-swept radiation, a splitter for splitting the multiplexed wavelength-swept radiation to a sample and a reference path, an optical detector for detecting an interference signal created by an optical interference between a reflection from the sample and light traversing the reference path, and a signal processing system which uses the interference signal to construct an image of the sample, wherein at least one of the N wavelength trajectories differs from another of the N wavelength trajectories with respect to at least one parameter of the group consisting of wavelength repetition rate, wavelength sweep speed, phase translation, and wavelength tuning range.

In a more specific embodiment of the present invention, the N VCLs are electrically pumped. In another specific embodiment of the present invention, the N VCLs are optically pumped. In yet another more specific embodiment of the present invention, the N VCLs have an integrated VCL optical pump. In one embodiment of the present invention, a single optical pump is used to pump all of the N VCLs.

In one embodiment of the present invention, a single optical amplifier is used to amplify the wavelength swept radiation. In one embodiment of the present invention, each VCL is monolithically integrated with an optical amplifier.

In one embodiment of the present invention, the N vertical cavity lasers are monolithically integrated on a common substrate.

In one embodiment of the present invention, at least one of the N vertical cavity lasers is a MEMS-tunable VCL tuned by a voltage source. In a more specific embodiment of the present invention, every one of the N vertical cavity lasers is a MEMS-tunable VCL tuned by a voltage source.

In one embodiment of the present invention, exactly one of the N VCL tunable outputs is turned on at any one point in time. In a more specific embodiment of the present invention, each of the N vertical cavity lasers is electrically pumped, and each of the N VCL outputs is turned on and off by control of an electrical pumping drive current.

In one embodiment of the present invention, each of the N vertical cavity lasers is repetitively swept at a different wavelength repetition rate. In one embodiment of the present invention, each of the N vertical cavity lasers is swept over a different wavelength bandwidth. In one embodiment of the present invention, a VCL swept over a smaller wavelength bandwidth is used for longer range imaging, and a VCL swept over a larger wavelength bandwidth is used for shorter range imaging. In one embodiment of the present invention, a VCL at a slower repetition frequency is used for longer range imaging, and a VCL at a faster repetition frequency is used for shorter range imaging.

In one embodiment of the present invention, each of the N vertical cavity lasers is driven by a single tuning waveform having a first wavelength repetition frequency, each of the single tuning waveforms is a phase-translated copy of another of the single tuning waveforms, and the multiplexed wavelength-swept radiation has a second wavelength repetition frequency that is N times the first wavelength repetition frequency.

In one embodiment of the present invention, the N vertical cavity lasers include a first VCL emitting a first VCL output over a first VCL wavelength range, and a second VCL emitting a second VCL output over a second VCL wavelength range, wherein the total wavelength range is a combination of the first and second VCL wavelength ranges.

In one embodiment of the present invention, at least one of the N vertical cavity lasers is driven at a mechanical resonance of a MEMS structure. In one embodiment of the present invention, at least one of the N vertical cavity lasers is driven in a vacuum environment. In one embodiment of the present invention, each of the N vertical cavity lasers is driven at a mechanical resonance of a MEMS structure. In one embodiment of the present invention, the system further comprises a first MEMS-VCL having a first mechanical resonance frequency, and a second MEMS-VCL having a second mechanical resonance frequency substantially different from the first mechanical resonance frequency. In one embodiment of the present invention, each of the N vertical cavity lasers is in a vacuum environment. In a more specific embodiment of the present invention, the vacuum environment is provided by an evacuated butterfly package. In another more specific embodiment of the present invention, the vacuum environment is provided by an evacuated transistor outline package.

In one embodiment of the present invention, the maximum driving voltage of the voltage source is less than 10V.

In one embodiment of the present invention, the total wavelength range is contained within a range of about 750 nm-900 nm. In another embodiment of the present invention, the total wavelength range is contained within a range of about 950 nm-1150 nm. In yet another embodiment of the present invention, the total wavelength range is contained with a range of about 1200-1650 nm. In another embodiment of the present invention, the total wavelength range is contained within a range of about 1700-2300 nm.

In one embodiment of the present invention, the sample is a human eye. In one embodiment of the present invention, the image includes a portion of an anterior eye and a portion of a retina of a human eye. In one embodiment of the present invention, the sample includes human tissue. In another embodiment of the present invention, the sample includes animal tissue.

A further understanding of the nature and advantages of the present invention may be realized by reference to the remaining portions of the specifications and drawings.

DETAILED DESCRIPTION OF PREFERRED AND ALTERNATE EMBODIMENTS

Figure 1:
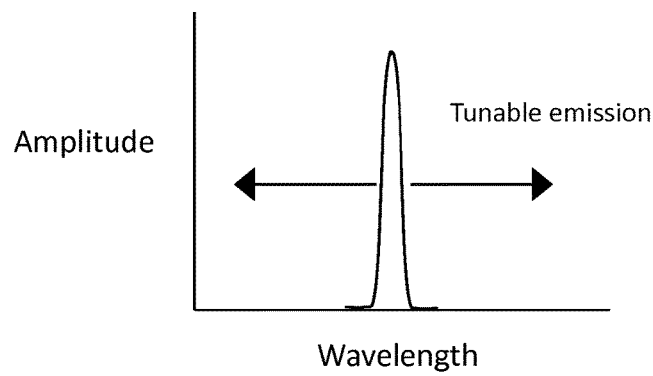
FIG. 1 is a plot showing wavelength tuning of tunable laser or widely tunable laser.
Figure 2:
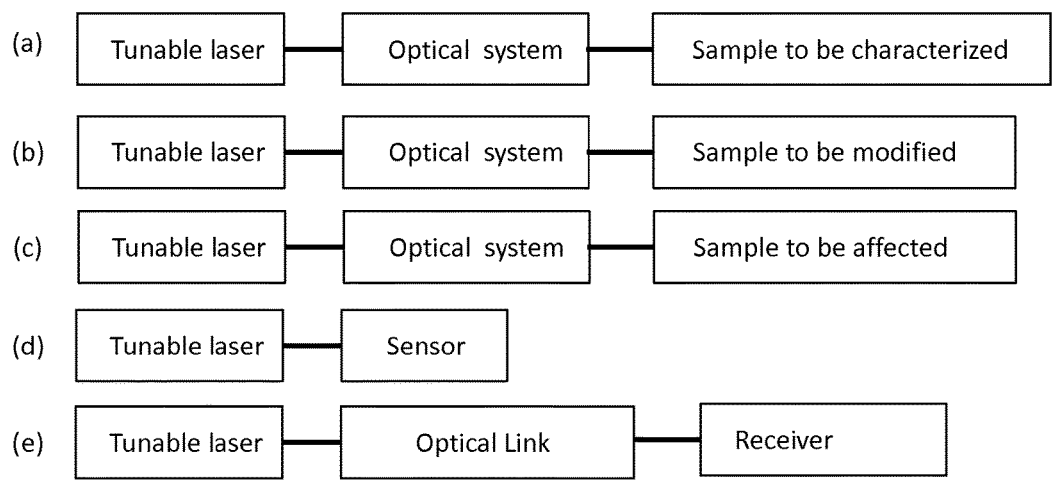
FIG. 2 is a collection of block diagrams shoving example applications of tunable lasers.
Figure 3:
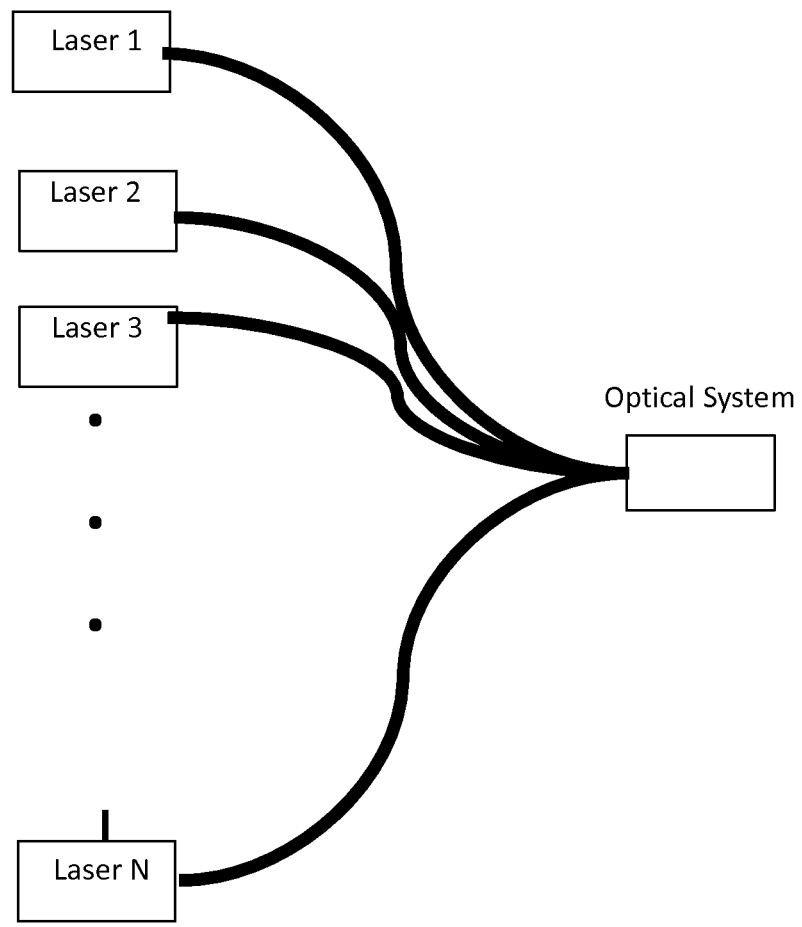
FIG. 3 is a diagram shoving a Laser Array.
Figure 4:
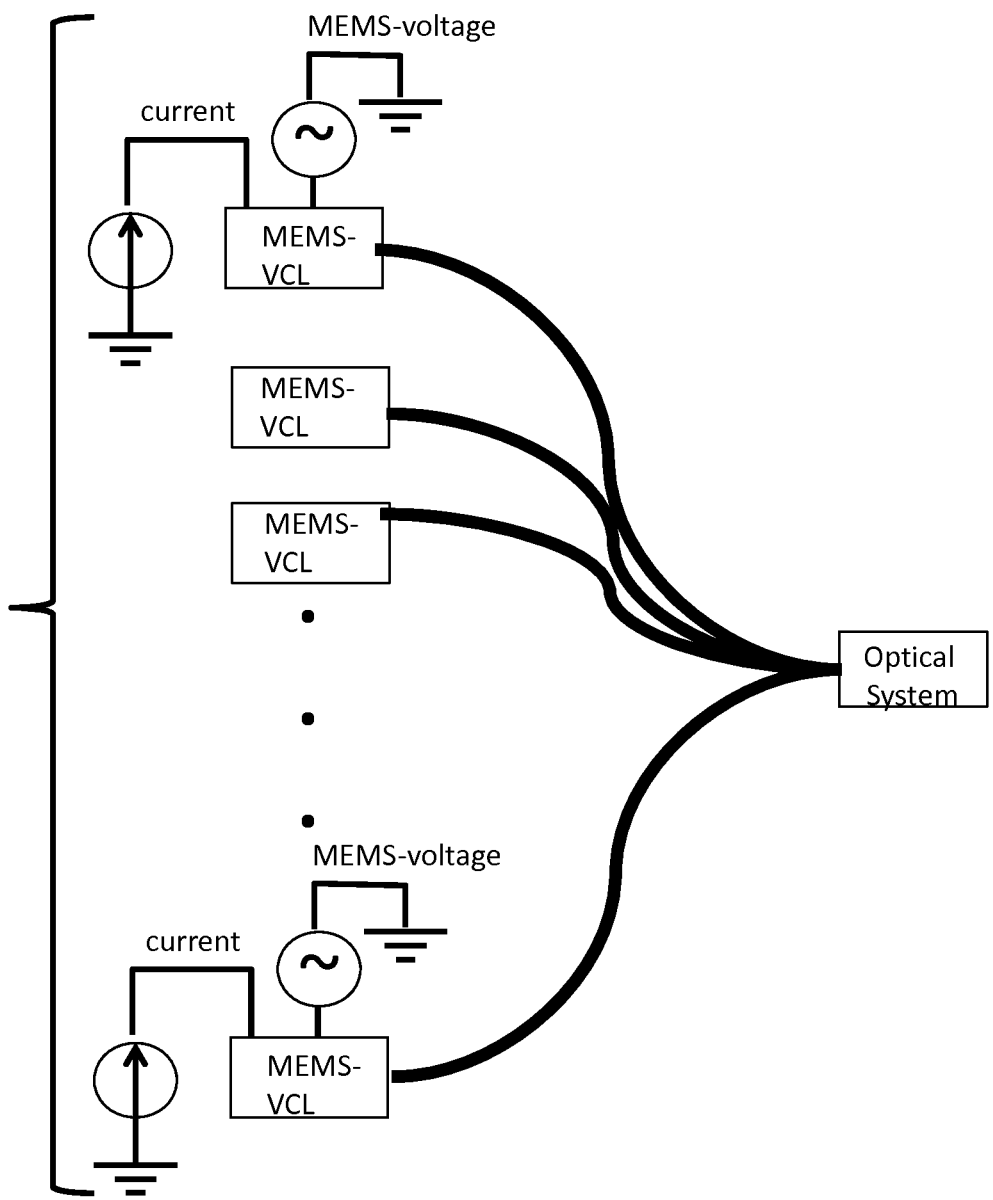
FIG. 4 is a diagram shoving an array of electrically pumped MEMS-VCLs.
Figure 5:
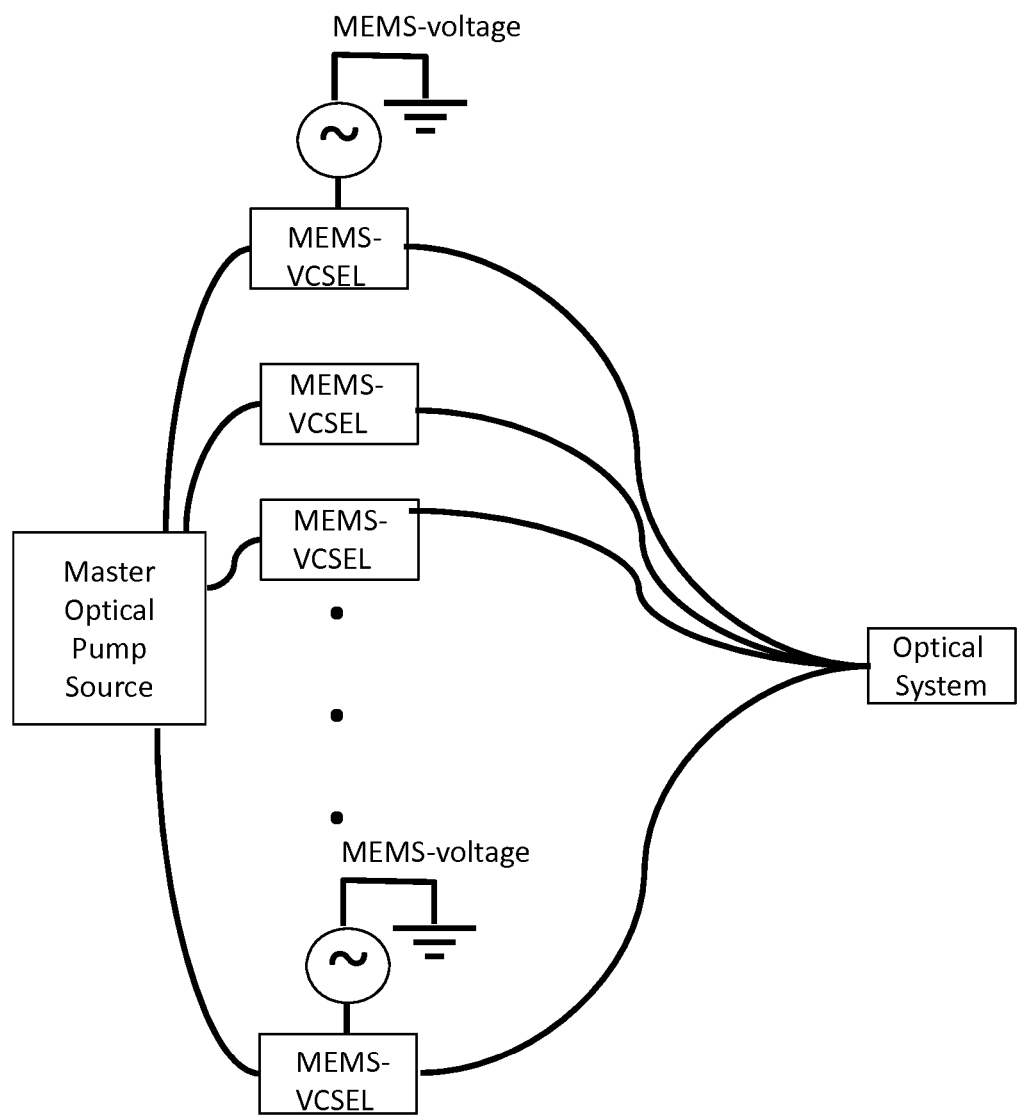
FIG. 5 is a diagram showing an array of optically pumped MEMS-VCLs.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

This disclosure describes the best mode or modes of practicing the invention as presently contemplated. This description is not intended to be understood in a limiting sense, but provides an example of the invention presented solely for illustrative purposes by reference to the accompanying drawings to advise one of ordinary skill in the art of the advantages and construction of the invention. In the various views of the drawings, like reference characters designate like or similar parts.

Figure 6:
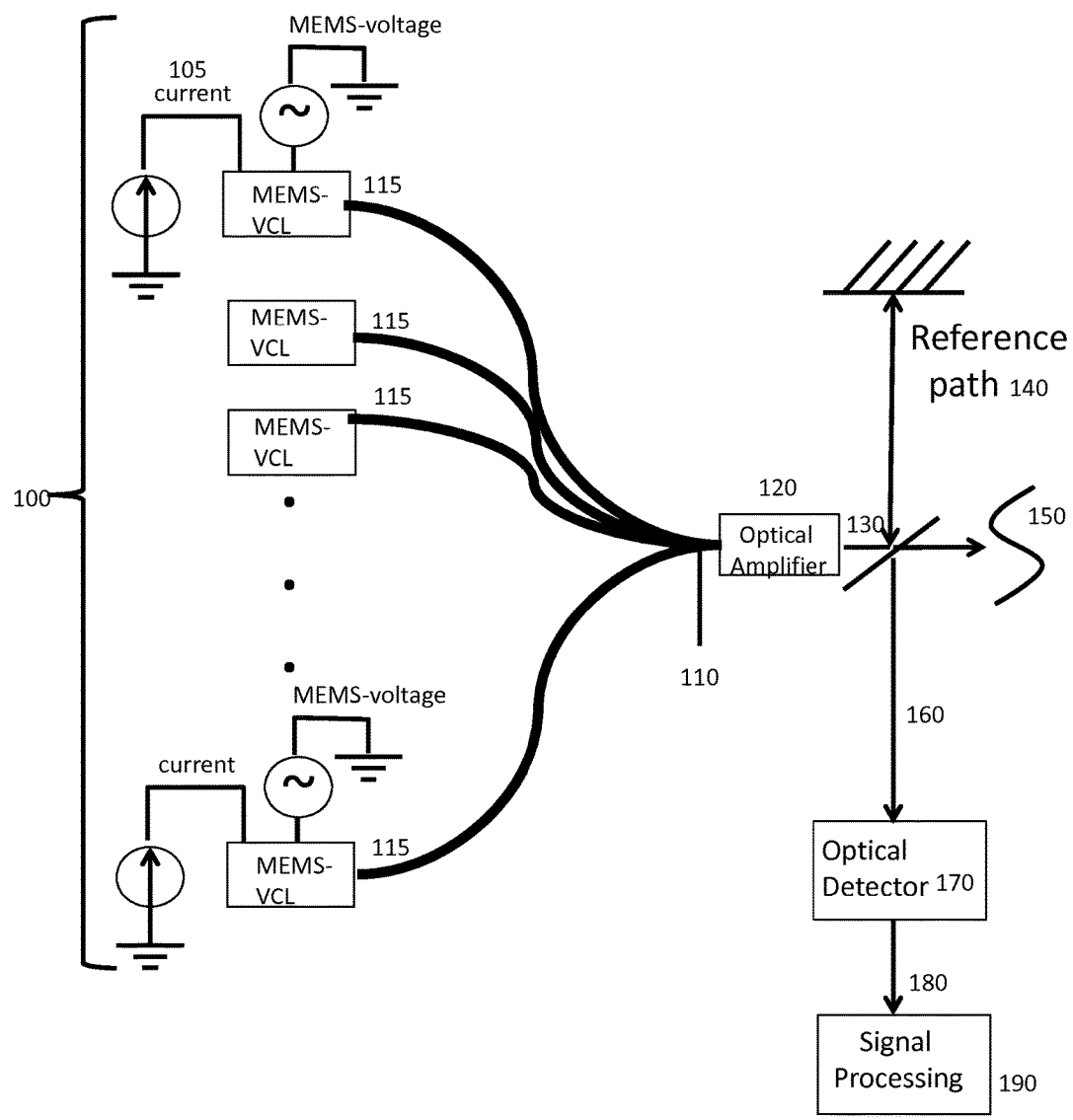
FIG. 6 is a diagram showing an array of electrically pumped MEMS-VCLs used in an OCT imaging system.

FIG. 6 shows a schematic of a preferred embodiment of the present invention in the context of a swept source OCT imaging system. An array of N electrically pumped tunable VCSELs 100 driven by N current sources 105. The series of VCLs emits N outputs 115, which are combined into a single optical fiber 110. The combined outputs 115 in the fiber 110 are amplified by a single optical amplifier 120, which is preferably a semiconductor optical amplifier, but could be any optical amplifier such as a fiber amplifier. Ideally the VCLs are wafer-scale fabricated and monolithically integrated on a common substrate such as 1050 nm VCLs on a GaAs substrate or wafer-bonded 1310 nm VCLs on a GaAs substrate, as described in (V. Jayaraman, G. D. Cole, M. Robertson, A. Uddin, and A. Cable, "High Sweep Rate 1310 nm MEMS-VCSEL with a 150 nm continuous tuning range," *Electronics Letters*, May 5, 2012.) and in (V. Jayaraman, G. D. Cole, M. Robertson, C. Burgner, D. John, A. Uddin, and A. Cable, "Rapidly-swept Ultra-widely tunable 1060 nm MEMS-VCSELs," *Electronics Letters*, Sep. 6, 2012). The VCLs may all be essentially the same devices, or a collection of different devices drawn from the large design space that includes but is not limited to substantially differing wavelengths, output powers, coherence lengths, tuning ranges, intensity noise, wavelength jitter, polarization state, or the multitude of other parameters that would be characteristics commonly associated with laser devices. The VCLs could also be diced from separate wafers and mounted on a single sub-carrier, or could be individually packaged VCLs. The combination of a series of VCLs produces a highly adaptable VCL System that would find many applications such as spectroscopy, interventional medicine, and non-invasive imaging. While there is a multitude of applications well beyond these three example markets, the non-invasive imaging market will be used as one exemplary application.

For the OCT imaging application, the amplified output 130 is split to a reference path 140 and a sample 150. Reflected tight from the sample and light traversing the reference path are combined in a single optical path 160 and impinge on an optical detector 170. The detector 170 generates an interference signal 180, which is processed by a signal processing system 190 to generate a depth profile of the sample 150. Although the reference path shown in FIG. 6 involves back-reflection off a mirror, the reference path could also be implemented as a simple optical delay. The system of FIG. 6 may include many other elements such as x-y scanning to create 2 and 3-dimension images of the sample 150. In a preferred embodiment, each VCL of the array 100 is a MEMS-tunable VCL driven by a voltage drive, but in alternate embodiments the VCL could be tuned by a piezo or by an intra-cavity refractive index tuning element like a liquid crystal, and more generally any optical, electro-optic, or electro-optomechanical device. Additionally, for some applications it would be advantageous to combine one or more VCSELs with one or more non VCSEL, sources; external cavity semiconductor swept laser sources, tunable fiber lasers, and fixed wavelength sources both VCL and non VCL. The preferred embodiment of FIG. 6 could be replaced by alternate embodiments in which one or more VCL outputs have separate optical amplifiers, or in which the optical fibers are replaced by free-space optical paths. Additionally, some application may benefit from one or more VCLs being maintained on one or more optical fibers so as to allow some arbitrary subsets of the collection of Vas to be directed for uses somewhat separately from the remaining VCLs.

Figure 7:
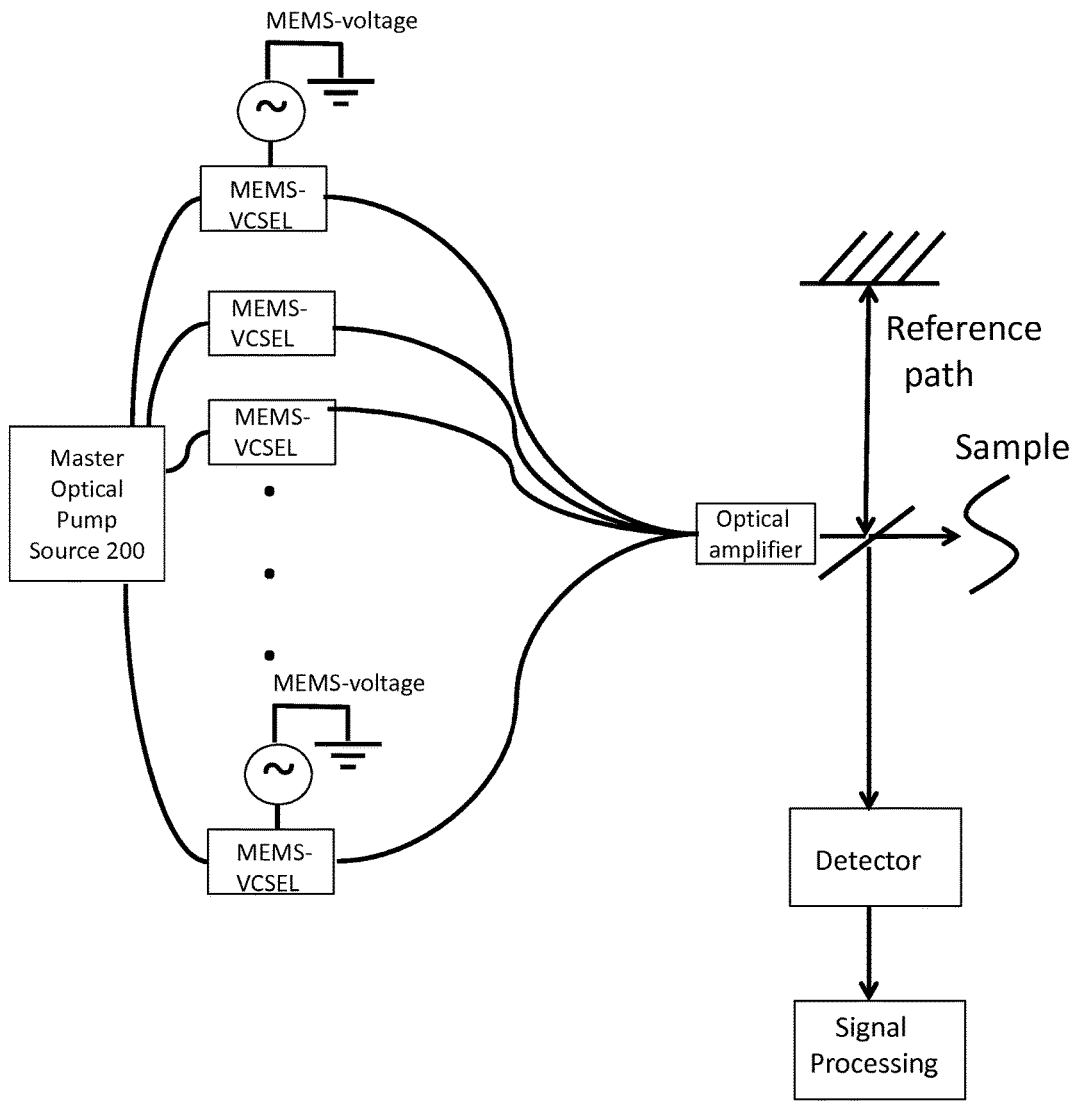
FIG. 7 is a diagram showing an array of optically pumped MEMS-VCLs used in an OCT imaging system.

FIG. 7 illustrates an alternate embodiment in the context of OCT employing optically pumped VCLs using a single master optical pump 200. Other embodiments could use a separate optical pump for each VCL, such as an integrated VCL optical pump as described in (V. Jayaraman, T. J. Goodnough, T. L. Beam, F. M. Ahedo, and R. A. Maurice, "Continuous wave operation of single transverse mode 1310 nm VCSEL up to 115 C," *IEEE Photonics Technology Letters* vol. 12, no. 12, December, 2000.)

The VCL arrays of FIGS. 6 and 7 can be employed in a variety of ways to create a multiplexed wavelength-swept radiation in the common optical fiber 110 enabling higher speed, higher resolution, or more flexible SS-OCT. For example, each VCL could be overdriven, with only a desired portion of the wavelength trajectory used for imaging. Using a tunable filter within the Swept VCL that has a free spectral range that is significantly larger than what is required to scan across the bandwidth of the VCL it is possible to achieve a duty factor (swept laser tuning period to total period of the system) that could be varied from a few percent to nearly 100%. Using a series of such VCLs configured as in FIG. 6 it is then possible to stitch together a series of individual VCL scans within the larger total period. Such a system would provide from the use of one, more than one, or all of the series of VCLs of FIG. 6.

Figure 8:
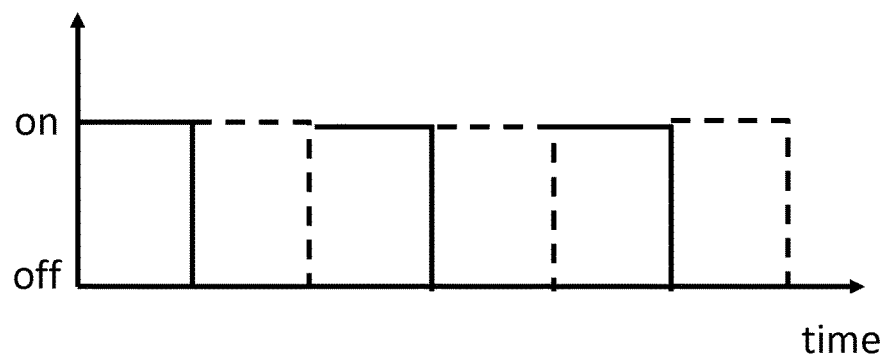
FIG. 8 is a collection of plots showing interleaving of multiple VCLs to achieve high repetition rate and duty cycle.
Figure 8:
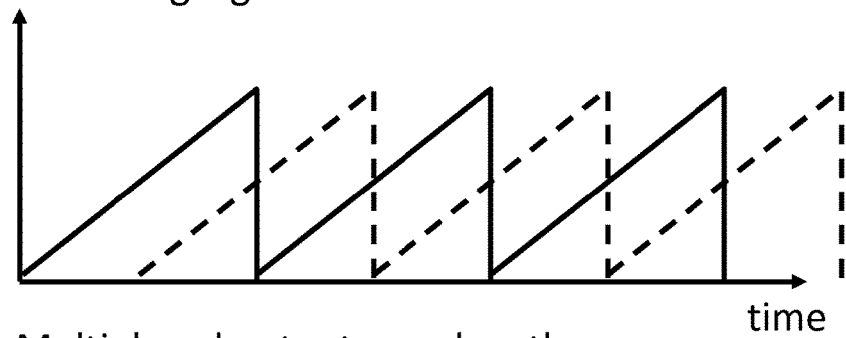
Figure 8:
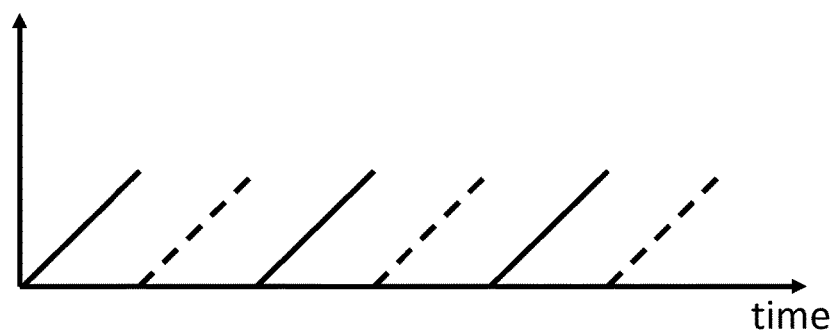

This is particularly advantageous in vacuum where very large deflections encompassing more than one free spectral range of a VCL cavity can be obtained with low voltages, as discussed in (G. D. Cole, J. E. Bowers, K. L. Turner, and N. C. McDonald, "Dynamic Characterization of MEMs-Tunable Vertical-Cavity SOAs," IEEE/LEOS International Conference on Optical MEMS and Their Applications (MOEMS 2005), Oulu, Finland, 1-4 Aug. 2005.) Under such operation, the VCL is turned on only during a useful portion of a wavelength sweep and turned off during an undesired portion of the wavelength sweep. In the preferred embodiment, the VCL is an electrically pumped VCL turned on and off by control by control of the drive current 105. A representative example of typical drive waveforms for the case of an array of two electrically pumped VCLs is shown in FIG. 8. Waveforms for a first VCL 1 are shown solid and those associated with a second VCL 2 are shown dashed. Each VCL is over-driven by a substantially identical but phase-translated waveform, as shown in FIG. 8B. The multiplexed output in the common optical fiber 110, shown in FIG. 8C, contains a wavelength sweep from both VCLs at twice the repetition period of that for a single VCL, with nearly 100% duty cycle. The individual VCLs 1 and 2 are turned on and off at the appropriate times by drive current waveforms shown in FIG. 8A. It should be appreciated that there are numerous ways to achieve substantially the result shown in FIG. 8C, for example if the FSR of the tuning portion of the VCL is substantially larger than the tuning range of the VCL then turning on and off as shown in FIG. 8A would not be required. Hence it is our intention to describe the general operation of VCL Array to emphasize its usefulness with the understanding that there are many modes of operation for the VCL Array.

Figure 9:
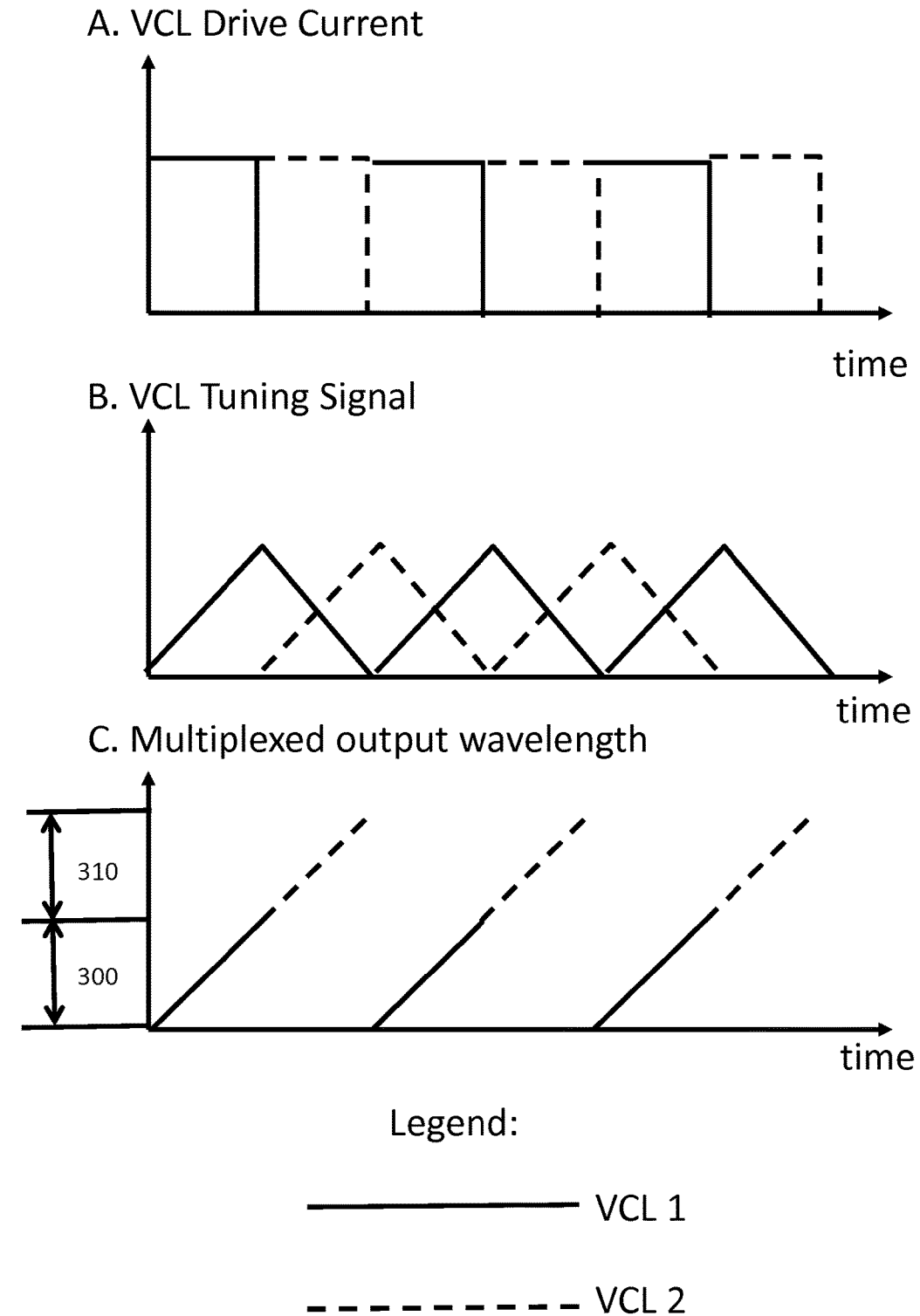
FIG. 9 is a collection of plots showing interleaving of multiple VCLs to achieve a multiplexed output wavelength.

The example of FIG. 8 illustrates a case where each of the VCL outputs 115 is scanned over an essentially identical wavelength range. FIG. 9 illustrates waveforms for another preferred embodiment employing a first electrically pumped VCL emitting over a first wavelength range 300, and a second electrically pumped VCL emitting over a second wavelength range 310, as shown in FIG. 9C. Each VCL is bi-directionally tuned over its wavelength range as shown by the tuning waveforms in FIG. 9B. Each VCSEL is also turned on and off as shown by drive current waveforms in FIG. 9A. The net result is a wavelength range in the multiplexed output in fiber 110 that is a combination of the first wavelength range of VCL 1 and the second wavelength range of VCL 2, as shown in FIG. 9C. As with all the examples in this work, the array of lasers could be any combination of electrically pumped VCL, optical pumped VCL, or non-VCL swept or fixed laser sources. Where the output of the array of lasers is either maintained separately in free space, or in an optical fiber, or combined with one of more of the other lasers in the array for subsequent use in a larger system or application.

Figure 10:
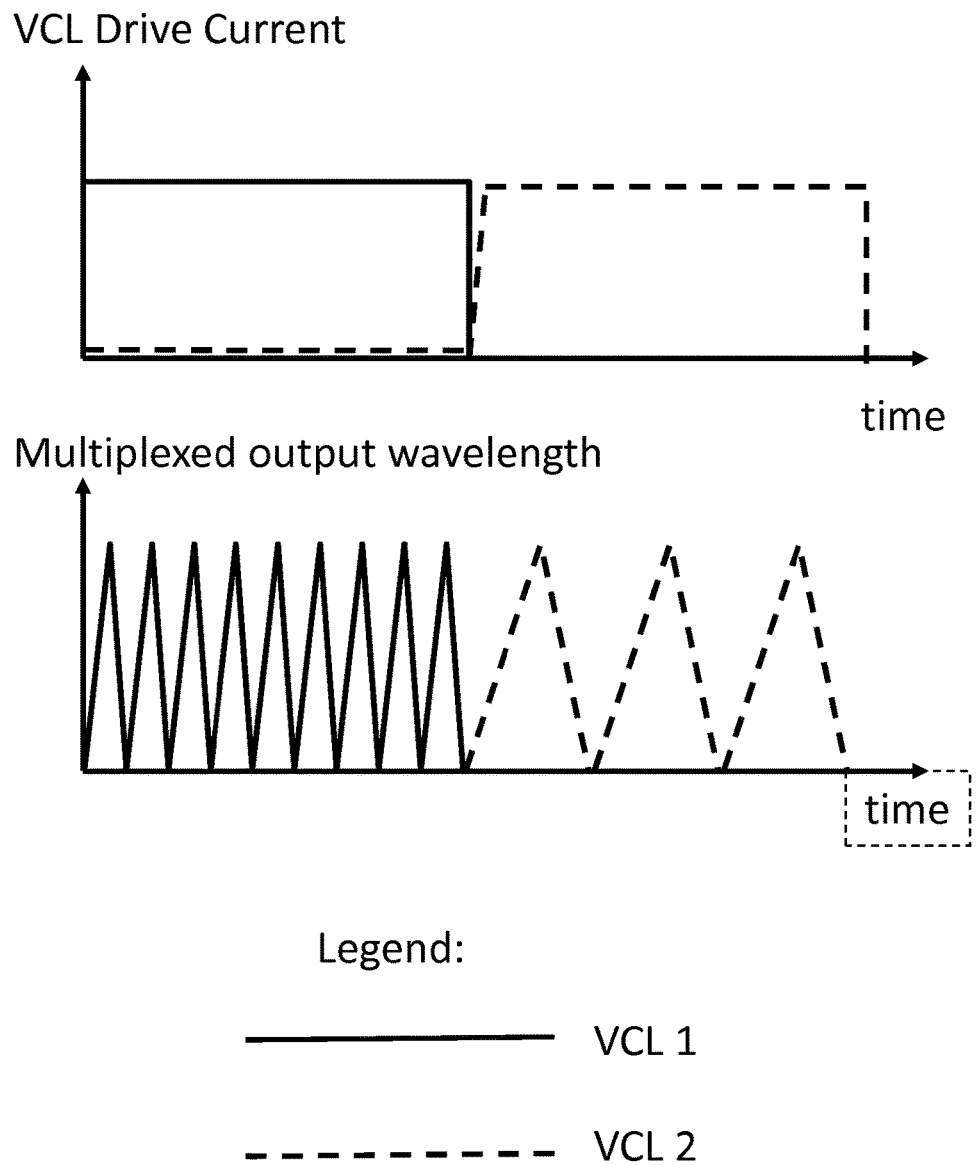
FIG. 10 is a collection of plots showing interleaving of multiple VCLs to achieve different sweep repetition rates.

FIG. 10 illustrates another preferred embodiment in which a first and second VCL are driven over an identical wavelength range, but at two wavelength repetition rates, to enable short range high speed imaging and long range low-speed imaging, respectively. Only VCL 1 is turned on for a period of time to acquire a first image, and only VCL 2 is turned on for a certain period of time to acquire a second image. Alternately, the two VCLs could be on simultaneously, and the two signals deconvolved in electronics, if the interference signals generated by both VCLs fall in non-overlapping frequency bands. In the ideal embodiment, both VCL 1 and VCL 2 have different mechanical resonances and each is driven in a vacuum environment provided by an evacuated hermetic package such as a butterfly package. Alternatively, VCL 1 and VCL2 could be on simultaneously but with non-overlapping wavelength scan ranges that are separated enough to allow an optical element such as a dichroic or wavelength selective beamsplitter to separate the signals at the appropriate point for the given application. Another alternative would be the use of two VCLs that overlap in both time and wavelength tuning range, but are different polarizations so as to allow a polarization beamsplitter to be used to separate the two VCL sources. A skilled person can no doubt now understand, the VCL Array acts as a highly adaptable laser system that can be employed in a multitude of applications providing substantial benefits over conventional laser systems.

Figure 11:
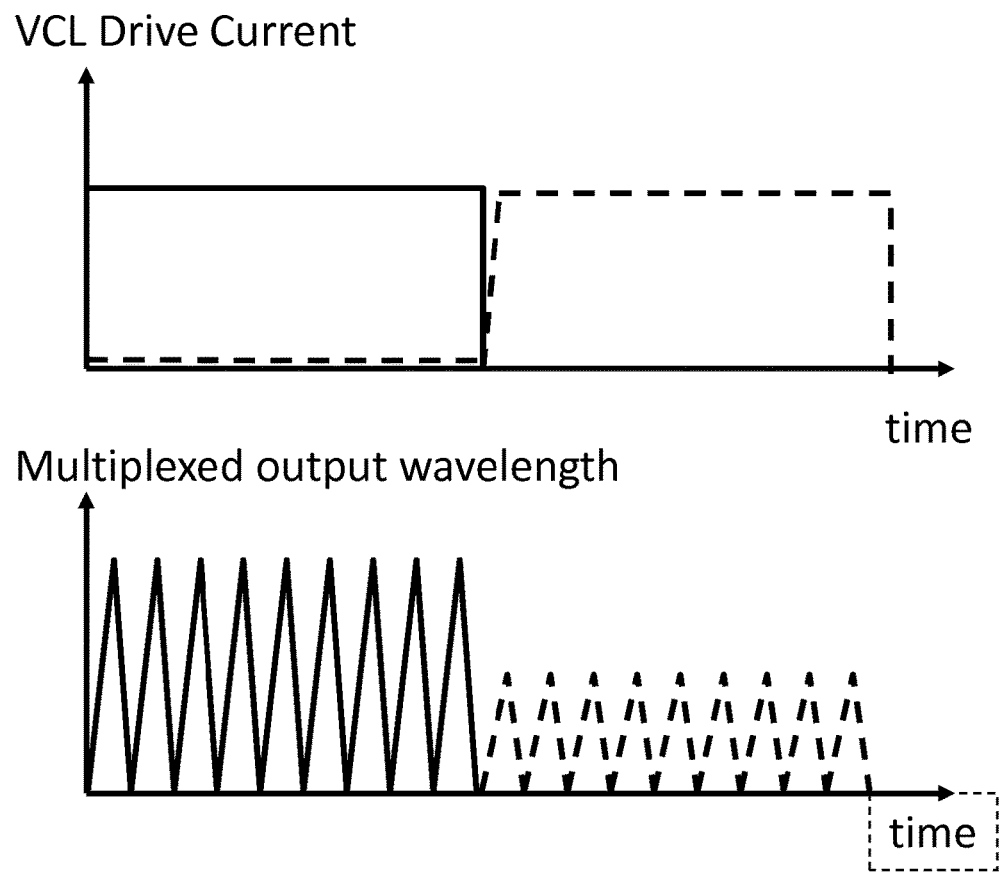
FIG. 11 is a collection of plots shooting interleaving of multiple VCLs to achieve different options for sweep range.

FIG. 11 illustrates another preferred embodiment in which a first VCL is driven over a wide tuning range and a second VCL is driven over a narrow tuning range, to again enable short range high resolution imaging or longer range lower resolution imaging. The approaches of FIGS. 10 and 11 could be combined to have each VCL operate not only over a different wavelength bandwidth but also at a different wavelength repetition frequency. Only one VCSEL is on at a particular time to enable one imaging mode at each time.

Figure 12:
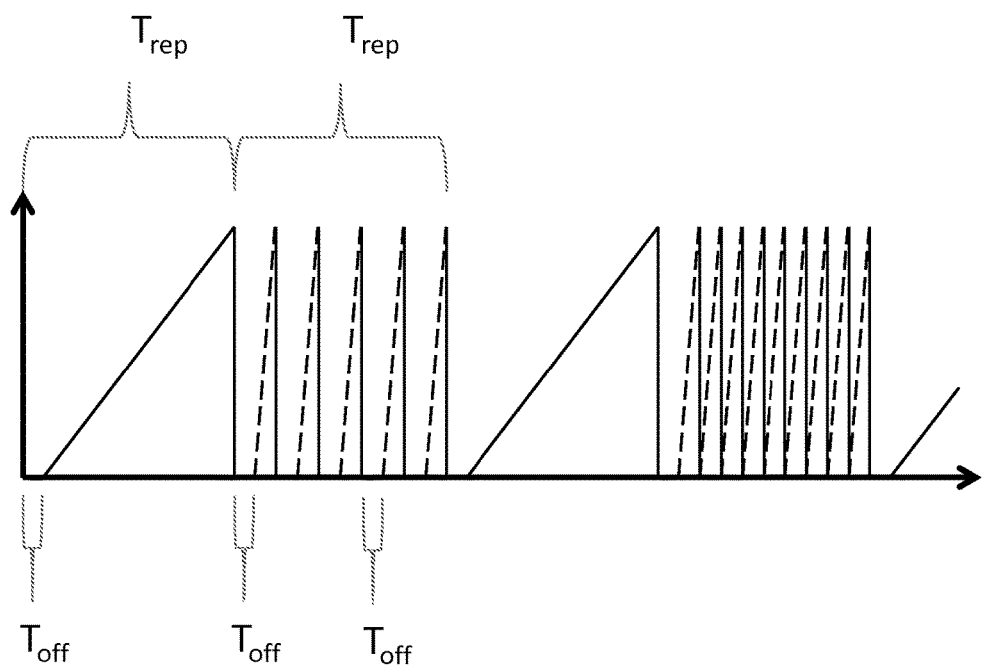
FIG. 12 is a collection of plots showing interleaving of multiple sweeps to achieve long range region of interest (ROI) searching capability to track an object with sweeps to perform fast and shorter range imaging using an OCT imaging system.

FIG. 12 illustrates another preferred embodiment in which the system is configured to capture 3D images of moving samples. VCL 1 is driven over a tuning range with a sample interval that supports a long imaging range. This VCL 1 is used to locate a region of interest (ROI) and to provide periodic updates as to movement of the sample. For some applications a single A-scan be used to obtain the location data. VCL 2 is then used to acquire the imaging data from the sample. The ratio of the number of location scans from VCL 1 to the number of imaging scans from VCL 2 can be adjusted as appropriate for the application. For slowly moving samples VCL 1 can be used to locate the sample in between a very large number of scans made by the imaging laser VCL 2. FIG. 12 is highly simplified as the ratio of imaging scans to location scans would typically be a significantly larger number than what is shown. Additionally, in the more general case there could be M location lasers and N imaging lasers so as to obtain a more complete understanding of the motion of the sample. The larger imaging system would then have facilities to compensate for the motion of the sample reported by the M location lasers. Assuming the sample is moving slowly then the imaging time could be substantially larger than the location time, hence one location laser could be routed around the sample so as to provide movement data in more than one dimension. The exact configuration of the system would be highly dependent upon the application, the benefits of this invention is its ability to be adapted to many different circumstances and imaging scenarios. In one embodiment for OCT imaging the reference arm length could be adjusted based on a measurement from the ROI finding, long range imaging sweep OCT information.

Figure 13:
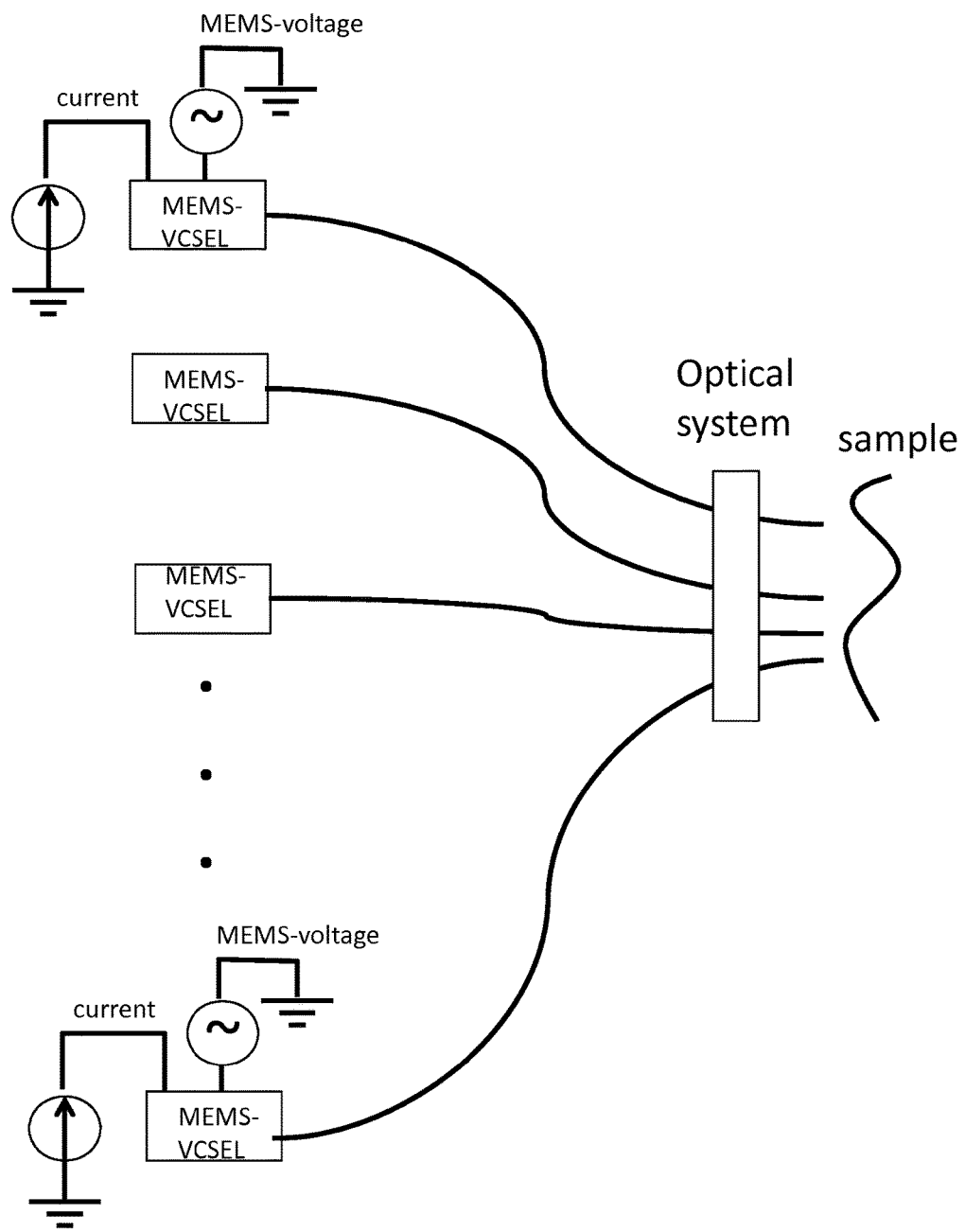
FIG. 13 is a diagram showing parallel point imaging using a laser array.

FIG. 13 illustrates another preferred embodiment of this invention for multi-beam optical coherence tomography, where multiple spatial locations are imaged simultaneously. Here, each VCL output is directed to a different physical location on a sample by the optics. In the case of imaging the eye, this is preferably done without optical amplification of each VCL, if each VCL is operated within a range of about 980-1120 nm, and emits fiber-coupled output power of about 15 mW. However, separate optical amplifiers can be used. The preferred embodiment would also use electrically pumped VCLs. In an alternate embodiment, each VCL would be optically amplified and/or optically pumped. The amplification could be provided by an integrated optical amplifier, integrated monolithically with each VCL, as described in (M. Nakahama, T. Shimada, and F. Koyama, "Lateral Integration of MEMS-VCSEL and slow light amplifier boosting single mode power," IEICE Electronics Express, vol. 9, no. 6, pp. 544-551, 2012.). For operation near 1310 nm and for imaging highly scattering tissue, optical amplification of each VCL is likely necessary. Integrated optical pumping could be accomplished as done previously in (V. Jayaraman, T. J. Goodnough, T. L. Beam, F. M. Ahedo, and R. A. Maurice, "Continuous wave operation of single transverse mode 1310 nm VCSEL up to 115 C," *IEEE Photonics Technology Letters* vol. 12, no. 12, December, 2000.)

The examples shown in FIGS. 8-12 show 2 VCLs, but this is for illustrative purposes only, and the concepts shown can be extended to N VCLs or to N non-VCLs or to any combination of VCL and non-VCL devices. In addition, through this specification and the claims which follow, the term VCL output is used to refer to amplified or non-amplified output, depending on the context. For example, VCL output of a VCL with an integrated amplifier refers to the amplified VCL output. While the examples shown in FIGS. 8-12 are explained in the context of OCT imaging, the essential sweep interleaving concepts are advantageous to other tunable laser applications and apply accordingly. For example, in a spectroscopy application, a long but coarsely sampled scan could be interleaved with rapid short scans to both monitor gross spectroscopic response over a long range of wavelengths at a longer time interval and rapidly updated and short time interval spectral response over particular wavelengths of interest. It is also possible to interleave two or more lasers with different scan wavelengths to achieve an extended wavelength sweep for spectroscopy.

In some applications, it may be desirable to combine swept and non-swept laser sources in the laser array. For example, it is possible to use a fixed wavelength probe beam that prepares a sample that is subsequently interrogated by a swept laser source.

For characterizing a sample's birefringent properties, it can be advantageous to probe the sample with light possessing different polarization states. The multiple lasers in the laser array can output different polarizations states into either a fiber optic or free space optical system. Switching between outputs of the different lasers changes the polarization state of the emission. Ability to impart different polarization states can be beneficial for polarization OCT, for example. Optical sensors, memory, storage devices, holographic devices, liquid crystal devices, and characterization/inspection equipment, such as that used for quality control, may use polarized light and benefit from fast polarization switching enabled by the laser array. Data transmission could also be encoded or compressed using polarization state for encrypted or improved throughput communication using swept or adjustable wavelength sources. In breath analysis one or more lasers would be used to monitor where in the breath cycle other data was taken from the other lasers in the laser array. Much like the movement tracking application describe herein, using a tracking laser to record the longer term respiration cycle, while making multiple spectroscopic measurements in parallel reduces the sampling errors inherent in the current measurement systems.

While this invention has been particularly shown and described with references to preferred and alternate embodiments thereof, it will be understood by those skilled in the art that various changes in form and details may be made therein without departing from the spirit and scope of the invention as defined by the appended claims. Also, while the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

The invention claimed is:

1. A system for swept source optical coherence tomography, the system comprising a light source emitting multiplexed wavelength-swept radiation over a total wavelength range, said light source comprising N wavelength-swept vertical cavity lasers (VCL) emitting N tunable VCL outputs having N wavelength trajectories, where N is greater than one, a combiner for combining said N tunable VCL optical outputs into a common optical path to create said multiplexed wavelength-swept radiation, a splitter for splitting said multiplexed wavelength-swept radiation to a sample and a reference path, an optical detector for detecting an interference signal created by an optical interference between a reflection from said sample and light traversing said reference path, and a signal processing system which uses said interference signal to construct an image of said sample, wherein at least one of said N wavelength trajectories differs substantially from another of said N wavelength trajectories with respect to at least one parameter of the group consisting of wavelength repetition rate, wavelength sweep speed, phase translation, and wavelength tuning range, wherein said N vertical cavity lasers include a first VCL emitting a first VCL output over a first VCL wavelength tuning range, and a second VCL emitting a second VCL output over a second VCL wavelength tuning range, wherein said total wavelength range comprises a combination of said first and second VCL wavelength tuning ranges.

2. The system of claim 1, wherein each of said N VCLs is electrically pumped.

3. The system of claim 1, wherein each of said N VCLs is optically pumped.

4. The system of claim 1, wherein each of said N VCLs has an integrated VCL optical pump.

5. The system of claim 3, wherein a single optical pump is used to pump all of said N VCLs.

6. The system of claim 1, wherein a single optical amplifier is used to amplify said wavelength swept radiation.

7. The system of claim 1, wherein each VCL is monolithically integrated with an optical amplifier.

8. The system of claim 1, wherein all of said N vertical cavity lasers are monolithically integrated on a common substrate.

9. The system of claim 1, wherein at least one of said N vertical cavity lasers is a microelectromechanical systems (MEMS)-tunable VCL tuned by a voltage source.

10. The system of claim 1, wherein every one of said N vertical cavity lasers is a MEMS-tunable VCL tuned by a voltage source.

11. The system of claim 1, wherein exactly one of said N VCL tunable outputs is turned on at any one point in time.

12. The system of claim 11, wherein each of said N vertical cavity lasers is electrically pumped, and each of said N VCL outputs is turned on and off by control of an electrical pumping drive current.

13. The system of claim 1, wherein each of said N vertical cavity lasers is repetitively swept at a different wavelength repetition rate.

14. The system of claim 1, wherein each of said N vertical cavity lasers is swept over a different wavelength bandwidth.

15. The system of claim 14, wherein a VCL swept over a smaller wavelength bandwidth is used for longer range imaging, and a VCL swept over a larger wavelength bandwidth is used for shorter range imaging.

16. The system of claim 13 wherein a VCL at a slower wavelength repetition frequency is used for longer range imaging, and a VCL at a faster wavelength repetition frequency is used for shorter range imaging.

17. The system of claim 1, wherein each of said N vertical cavity lasers is driven by a single tuning waveform having a first wavelength repetition frequency, each of said single tuning waveforms is a phase-translated copy of another of said single tuning waveforms, and said multiplexed wavelength-swept radiation has a second wavelength repetition frequency that is N times said first wavelength repetition frequency.

18. The system of claim 10, wherein at least one of said N vertical cavity lasers is driven at a mechanical resonance of a MEMS structure.

19. The system of claim 10, wherein at least one of said N vertical cavity lasers is driven in a vacuum environment.

20. The system of claim 10, wherein each of said N vertical cavity lasers is driven at a mechanical resonance of a MEMS structure.

21. The system of claim 10, further comprising a first MEMS-VCL having a first mechanical resonance frequency, and a second MEMS-VCL having a second mechanical resonance frequency substantially different from said first mechanical resonance frequency.

22. The system of claim 10, wherein each of said N vertical cavity lasers is in a vacuum environment.

23. The system of claim 19, wherein said vacuum environment is provided by an evacuated butterfly package.

24. The system of claim 19, wherein said vacuum environment is provided by an evacuated transistor outline package.

25. The system of claim 19, wherein a maximum driving voltage of said voltage source is less than 10V.

26. The system of claim 1, wherein said total wavelength range is contained within a range of about 750 nm-900 nm.

27. The system of claim 1, wherein said total wavelength range is contained within a range of about 950 nm-1150 nm.

28. They system of claim 1, wherein said total wavelength range is contained with a range of about 1200-1650 nm.

29. The system of claim 1, wherein said total wavelength range is contained within a range of about 1700-2300 nm.

30. The system of claim 1, wherein said sample is a human eye.

31. The system of claim 30, wherein said image includes a portion of an anterior eye and a portion of a retina of said human eye.

32. The system of claim 1, wherein said sample includes human tissue.

33. The system of claim 1, wherein said sample includes animal tissue.

* * * * *